(12) United States Patent
LaSalle et al.

(10) Patent No.: US 6,273,789 B1
(45) Date of Patent: Aug. 14, 2001

(54) METHOD OF USE FOR SUPERSONIC CONVERGING-DIVERGING AIR ABRASION NOZZLE FOR USE ON BIOLOGICAL ORGANISMS

(76) Inventors: Richard Todd LaSalle, 2287 McMillan St., Eugene, OR (US) 97405; Salvatore F. Crivello, III, 10615 Len St., Santee, CA (US) 92071; V. Kim Kutsch, 1155 Twin Hills Dr., Jeffferson, OR (US) 97352

( * ) Notice: Subject to any disclaimer, the term of this patent is extended or adjusted under 35 U.S.C. 154(b) by 0 days.

(21) Appl. No.: 09/359,552

(22) Filed: Jul. 22, 1999

(Under 37 CFR 1.47)

Related U.S. Application Data

(62) Division of application No. 08/821,976, filed on Mar. 13, 1997, now Pat. No. 5,957,760.
(60) Provisional application No. 60/013,623, filed on Mar. 14, 1996.

(51) Int. Cl.[7] .............................. B24B 1/00; A61C 3/25
(52) U.S. Cl. ...................... 451/38; 451/40; 451/102; 433/88; 433/89; 433/125; 433/216
(58) Field of Search ................... 239/336, 379; 433/88, 125, 80, 89, 216; 451/36, 38, 39, 40, 90, 102

(56) References Cited

U.S. PATENT DOCUMENTS

| | | | |
|---|---|---|---|
| 1,703,029 | * | 2/1929 | Fairchild .............................. 451/102 |
| 2,744,361 | * | 5/1956 | Larson et al. . |
| 3,852,918 | * | 12/1974 | Black . |
| 4,218,855 | | 8/1980 | Wemmer . |
| 4,369,607 | * | 1/1983 | Bruggeman et al. . |
| 4,412,402 | * | 11/1983 | Gallant . |
| 4,462,803 | | 7/1984 | Landgraf et al. ...................... 433/88 |
| 4,478,368 | | 10/1984 | Yie ....................................... 239/430 |
| 4,492,575 | | 1/1985 | Mabille ............................... 433/88 |
| 4,569,161 | | 2/1986 | Shipman . |
| 4,595,365 | * | 6/1986 | Edel et al. . |
| 4,633,623 | | 1/1987 | Spitz . |
| 4,676,749 | | 6/1987 | Mabille ............................... 433/88 |
| 4,843,770 | | 7/1989 | Crane et al. . |
| 4,941,298 | | 7/1990 | Fernwood et al. . |
| 5,036,631 | | 8/1991 | Stoltz . |
| 5,050,805 | | 9/1991 | Lloyd et al. ......................... 239/424 |
| 5,099,619 | | 3/1992 | Rose . |
| 5,275,486 | | 1/1994 | Fissenko ............................... 366/177 |
| 5,275,561 | | 1/1994 | Goldsmith ............................ 433/216 |
| 5,283,985 | | 2/1994 | Browning . |
| 5,283,990 | | 2/1994 | Shank, Jr. . |
| 5,286,331 | | 2/1994 | Chen et al. ........................... 156/345 |
| 5,390,450 | | 2/1995 | Goenka ................................. 451/75 |
| 5,531,634 | * | 7/1996 | Schott . |
| 5,545,073 | * | 8/1996 | Kneisel et al. .................... 451/102 X |
| 5,601,478 | * | 2/1997 | Mesher ............................ 451/102 X |
| 5,865,620 | * | 2/1999 | Kutsch ................................. 433/88 |

OTHER PUBLICATIONS

Douglas, Deborah D., "Micro air abrasion gains acceptance as alternative cavity prep technique," *AGD Impact*, Oct. 1994, pp. 7 and 8.

Goldstein, Ronald E. DDS and Parkins, Frederick M. DDS, MSD, Ph.D, "Using Air–Abrasive Technology to Diagnose and Restore Pit and Fissure Caries," *JADA*, Article 2, vol. 126, Jun. 1995, pp. 761–766.

* cited by examiner

*Primary Examiner*—Timothy V. Eley
(74) *Attorney, Agent, or Firm*—Lori M. Friedman

(57) ABSTRACT

A device for removing material from biological organisms by directing an abrasive fluid stream onto a surface of a biological organism. The device operates on a standard household pressure source and includes a converging-diverging nozzle that produces a super-sonic abrasive-laden air stream having a temperature that is harmless to the biological organism. The device operates at such a temperature without the use of external elements, such as additional heaters or coolers. The internal contour of the nozzle bore is variable and determines conditions, such as, for example, velocity, temperature and shape of the particle-laden air

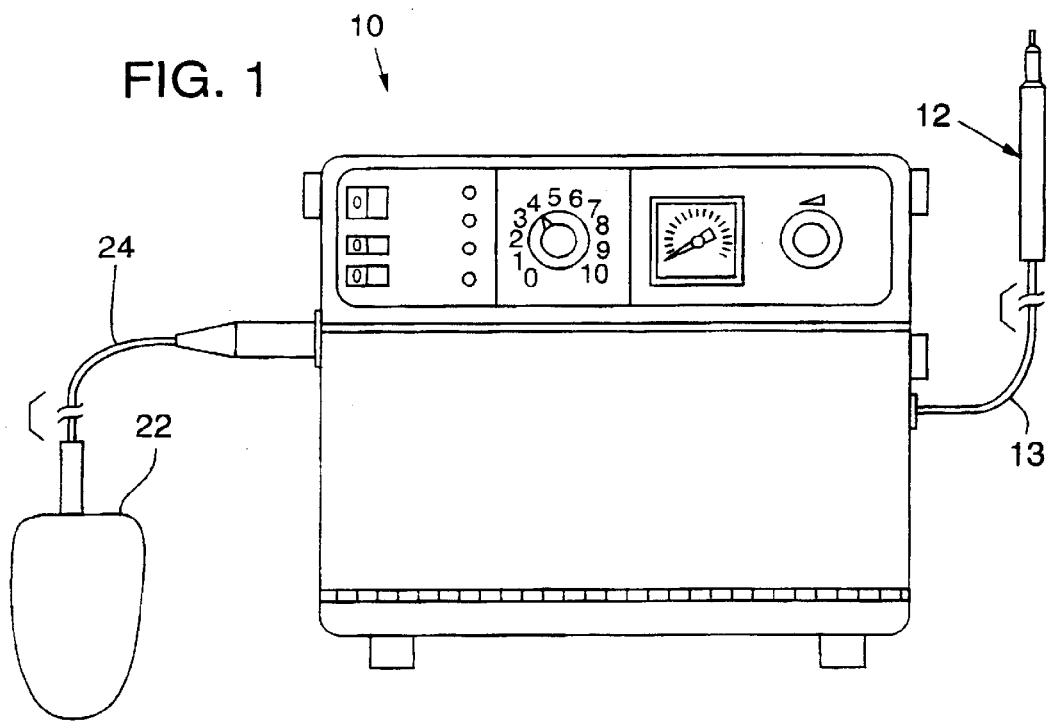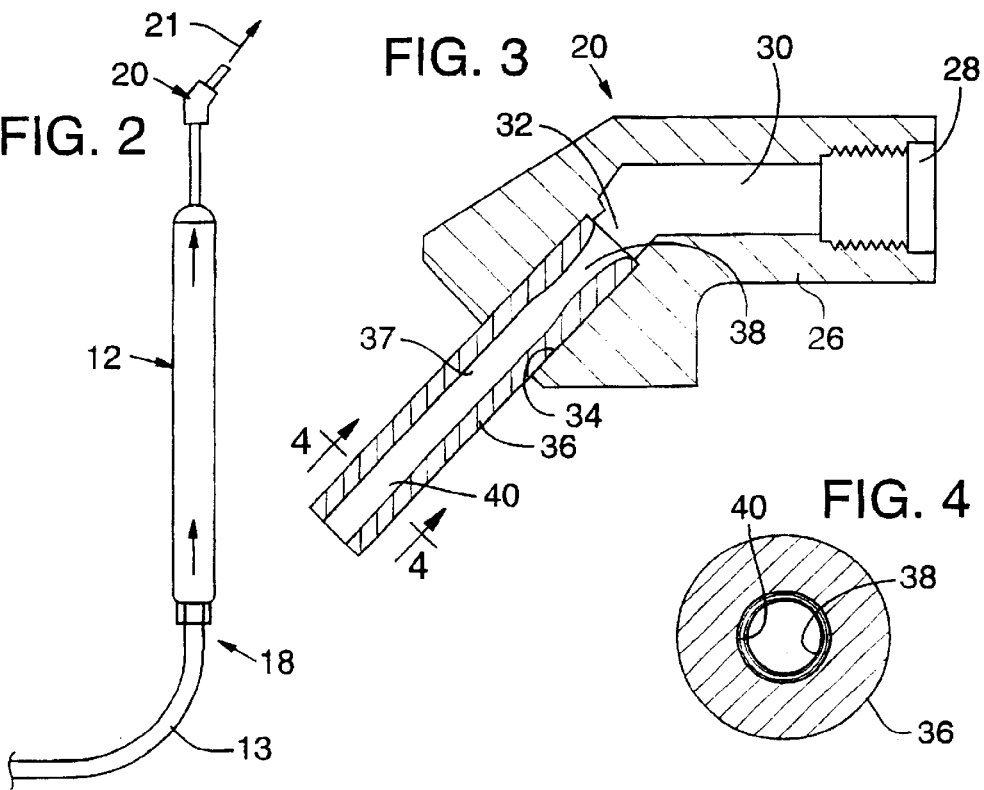

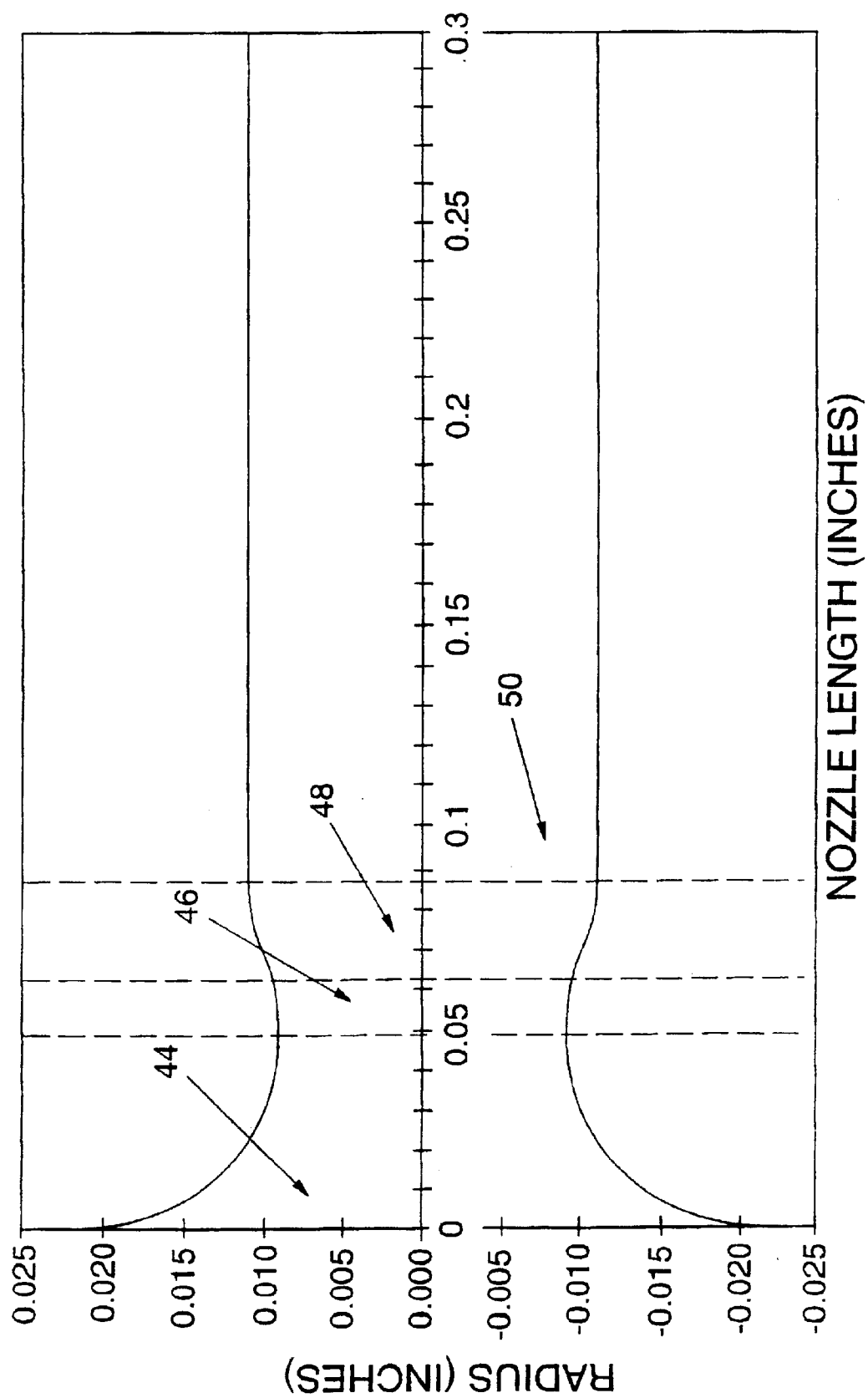

METHOD OF USE FOR SUPERSONIC CONVERGING-DIVERGING AIR ABRASION NOZZLE FOR USE ON BIOLOGICAL ORGANISMS

RELATED PATENT APPLICATIONS

This is a United States divisional patent application based on U.S. patent application Ser. No. 08/821,976 filed Mar. 13, 1997 now U.S. Pat. No. 5,957,760, which is based on provisional patent application 60/013,623 filed Mar. 14, 1996, entitled Supersonic Converging-Diverging Nozzle For Use On Biological Organisms.

TECHNICAL FIELD

The present invention relates to an air abrasion device and more particularly to an air abrasion nozzle that produces an abrasive-laden air stream to remove material from biological organisms.

BACKGROUND OF THE INVENTION

Air abrasion tools are becoming increasingly more popular for use on, for example, dental patients where an abrasive-laden fluid, such as air containing microscopic non-toxic abrasive powder, is directed onto one or more of the patient's teeth for quickly removing decay, preparing the teeth to receive fillings and/or for cleaning the teeth. Such abrasion devices provide advantages over conventional dental drills. For example, material is removed by pressurized abrasive air eliminating the heat, noise, and vibration produced by high speed drills. Also, the need for anesthesia is reduced because fluid used to cool the drill is eliminated. Furthermore, the risk of saliva contamination is reduced by maintaining a dry field. Air abrasion devices use a narrowly focused stream of particle-laden air that removes material from the tooth in proportion to various factors, such as, for example, the size and nature of the particle, the velocity of the particle on impact, and incident angle of impact of the particle. Because the cutting ability of the abrasive particle within the air stream is a function of the velocity of the particle, which in turn is a function of the air stream velocity, it is desirable to produce an air stream with very high velocity. Thus, the most effective method of increasing the material removal efficiency of the abrasive particles is to increase the air stream velocity.

Currently, the manufacturers of devices that accelerate particles to high speeds for abrasion and/or cutting on, for example, the tooth of a dental patient, use converging nozzles or constant area nozzles. Converging area or constant area nozzles can at best produce sonic flow velocities inside the nozzle and only slightly supersonic velocities just past the exit plane of the nozzle. For example, converging or constant area nozzles may produce a relatively low supersonic flow velocity of about Mach 1.2 for an extremely short distance past the exit plane of the nozzle. The velocity of the abrasive particles is controlled by the pressure difference across the nozzle. In order to achieve such a velocity of about Mach 1.2, a pressure of about 160 psig must be used. Most common dental office or household equipment can provide a reservoir gage pressure of up to about 80 psig. In order to achieve 160 psig, it is necessary to have an additional heavy duty compressor. This increases costs and takes up a considerable amount of space.

Another disadvantage of using such high pressure is that as the abrasive air fluid exhausts from the nozzle, the immediate drop in pressure causes the fluid to decrease in temperature. The static temperature of the fluid can decrease to, for example, about 20° Fahrenheit. Air flow of this temperature against a patent's tooth can cause extreme discomfort. In order to compensate for the coldness of the airstream and to increase patient comfort, an additional heater may be needed in order to heat the air. Another alternative to compensate for the coldness of the air stream would be to use an anesthetic which usually must be injected with a hypodermic needle.

These disadvantages can be overcome by the use of a converging-diverging (CD) nozzle. A CD nozzle consistently produces supersonic fluid velocities substantially above Mach 1 with a typical in-house source of pressurized air and at a temperature comfortable to the patient.

Converging-diverging nozzles have been known in heavy industry applications. For example, U.S. Pat. No. 5,390,450 discloses a supersonic converging-diverging exhaust nozzle to expel liquid $CO_2$ for cleaning a printed circuit board. This device coagulates the $CO_2$ snow into larger $CO_2$ snow particles and uses a supersonic nozzle operated in the overexpanded mode to focus the $CO_2$ snow onto the workpiece while reducing the noise produced by the pressurized exhaust.

U.S. Pat. No. 5,283,985 discloses a method of impacting abrasive particles against a surface to be treated using an internal burner by introducing the abrasive particles into the supersonic jet stream after expansion of combustion gases from the internal burner to nearly atmospheric pressure from very high pressures, and by causing the abrasive particles to accelerate through a nozzle having a length long enough to accelerate the particles to a much greater impact velocity.

U.S. Pat. No. 4,633,623 discloses a sandblasting nozzle to decontaminate radioactive members by means of a jet formed from a mixture of water and abrasive particles.

U.S. Pat. No. 5,283,990 discloses a sandblasting device that produces less turbulence as the blast media particles are accelerated through the nozzle that maintains maximum velocity of the blast media particles and cleaning rate during operation.

U.S. Pat. No. 5,275,486 discloses a nozzle in which a two-phase mixture of two fluids is accelerated by an expanded portion of the nozzle to supersonic velocity creating a one-phase mixture.

U.S. Pat. No. 5,050,805 discloses a supersonic nozzle in which the sound emitted by the nozzle is reduced to as low a level as possible to permit safe operation.

These prior devices are used in industrial applications such as sandblasting and operate at high pressures and/or at temperatures that are not applicable for use on biological organisms such as humans, plants and animals.

SUMMARY OF THE INVENTION

It is an object of the present invention to provide a supersonic air abrasion tool to more efficiently remove material from biological organisms.

Another object of the present invention is to provide an air abrasion tool capable of producing substantially high supersonic velocities.

A further object of the present invention is to provide an air abrasion tool that operates on a standard household pressure source.

Yet another object of the present invention is to provide an air abrasion tool that is operable at temperatures that are harmless to biological organisms without the use of external elements, such as additional heaters, coolers, or anesthetics.

Still a further object of the present invention is to provide a method of removing material from a biological organism with the use of a CD nozzle.

The present invention provides for a supersonic air abrasion tool for removing material from biological organisms such as humans, animals and plants. The nozzle of the present invention is a converging-diverging (CD) nozzle for directing an abrasive air stream against a surface of the biological organism and removing material therefrom. The internal contour of the nozzle bore determines conditions, such as, for example, velocity, temperature and shape of the particle-laden air stream and is designed to achieve greater cutting speeds at temperatures that do not harm the organism through pain, discomfort, or undue stress. The nozzle is designed so that the bore has four different sections. These sections cause the air stream to contract and expand which affects the velocity and temperature of the air stream. These sections include an elliptically converging section, a diverging expansion section, diverging compression section, and a parallel flow section. Thus, the internal contour of the nozzle bore is designed so that each section manipulates the air stream in order to obtain the precise desired air velocity and temperature without the aid of an additional pressure source or secondary influences such as cooling or heating elements applied or injected into the air stream inside the nozzle. Various nozzle designs may be employed to obtain specified conditions.

BRIEF DESCRIPTION OF THE DRAWINGS

Other objects features and advantages of the present invention will be apparent from the written descriptions and the drawings in which:

FIG. 1 is a pictorial diagram of an air abrasion cleaning system in accordance with the present invention.

FIG. 2 a side view of the hand piece containing the nozzle of the present invention.

FIG. 3 is a sectional view of the nozzle head shown with a nozzle inserted therein.

FIG. 4 is a cross-sectional end view of the axisymmetric nozzle of FIG. 3.

FIG. 5 is a graphic representation of the internal contour of the axisymmetric nozzle shown exaggerated for clarity.

DETAILED DESCRIPTION

Figure 6:
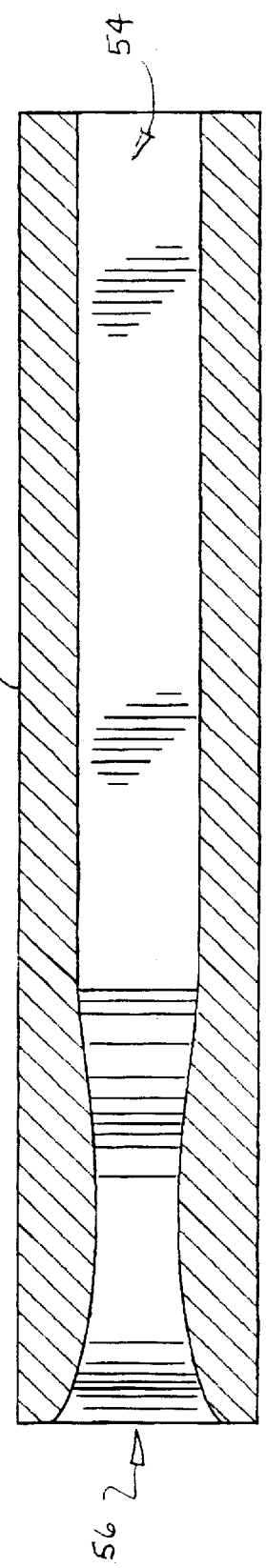
FIG. 6 is a cross-sectional side view of a planar nozzle.

An air abrasion system 10 in accordance with the present invention is illustrated generally in FIG. 1. A hand held air abrasion tool 12 is connected by a hose 13 through the system 10 to a reservoir of abrasive powder (not shown) and a source of compressed air (not shown). The abrasive powder is mixed with the compressed air in the system 10 in a manner known by those skilled in the art. The mixture of abrasive powder and compressed air form an abrasive-laden fluid that is directed through the hose 13 and the tool 12 onto the surface of an object for removing material from the object. One typical use is for directing the abrasive air stream onto the tooth of a dental patient to remove material, such as decay or amalgam. However, it is understood that this invention could be used to remove material from animals, such as, for example, removing portions of a horse's hoof. The invention can also be used to remove material from plants. The abrasive powder is typically a non-toxic abrasive such as aluminum oxide having particles with an average size of about 27.5 microns. The mixture of compressed air and abrasive powder forms an abrasive-laden fluid that flows from the hose 13 through an inlet 18 (FIG. 2) into the hand held tool and exits through a nozzle head assembly 20.

The source of air generally comprises an air compressor and reservoir of the type generally found in the medical environment such as a dentist's office. An air compressor of this type typically provides pressurized air within the range of about 60–80 psig. A foot-operated control 22 (FIG. 1) is connected to the system 10 through line 24 to activate the system 10 when depressed and deactivate the system 10 when released. When the system 10 is activated compressed air flows through it and may be regulated to the desired pressure. Then the abrasive powder may be added to the compressed air to form the abrasive-laden fluid. The system 10 may be used to control the air pressure, the amount of abrasive powder added to the air stream, and the operating characteristics of the system 10. The abrasive-laden fluid then travels through the hose 13 to the tool 12 and to the nozzle head assembly 20.

Referring now to FIG. 3, it can be seen that the nozzle head assembly 20 comprises a nozzle head 26 preferably made of aluminum having a counter bore 28 forming a sealed connection with the body of the tool 12 to allow the abrasive-laden fluid to remain pressurized as is well known in the art. A high pressure bore 30 is in fluid communication with the counter bore 28 and terminates in an exit bore 32 having a smaller cross-sectional configuration than the high pressure bore 30. The exit bore 32 may intersect the bore 30 at any desired angle. A supersonic converging-diverging nozzle 36 is coupled to the nozzle head 26 by inserting the distal end of the nozzle 36 into the exit bore 32 for directing the abrasive-laden fluid onto the surface of, for example, a tooth from which material is to be removed. The nozzle 36 is preferably made of tungsten carbide to withstand the severe abrasive action of the abrasive-laden fluid. The nozzle 36 has a variable bore 37 that is constructed to manipulate the abrasive-laden fluid to obtain the desired characteristics.

As seen most clearly in the graphical representation of FIG. 5, the nozzle bore 37 of this preferred embodiment is made up of four distinct sections that the abrasive-laden fluid must pass through in succession. The first section that the abrasive-laden fluid must pass through is an elliptically converging section 44 that is preferably about 0.05 inches (1.27 mm) long. The elliptically converging section 44 serves as an inlet to the nozzle bore 37. The second section of the nozzle bore 37 is formed by a circular-arc diverging expansion section 46 that is approximately 0.015 inches (0.381 mm) long. The diverging expansion section 46 then opens into a characteristic diverging compression section 48 that is about 0.023 inches (0.584 mm) long and forms the third section of the nozzle bore 37. Finally, the fourth section of the nozzle bore 37 is formed by a parallel-flow particle-acceleration section 50 that is approximately 0.212 inches (5.38 mm) long. The total length of the nozzle 36 in the preferred embodiment is about 0.30 inches (7.62 mm).

The method of operation will now be described with continuing reference to FIGS. 1–5. The abrasive-laden fluid flows from the tool 12 into the high pressure bore 30 within the nozzle head 26 through to the exit bore 30 and the nozzle 36. The abrasive-laden fluid is directed through the bore 37 and exits the bore 37 having a velocity with a Mach number of approximately 1.70.

The abrasive-laden fluid substantially increases its velocity as it passes through the nozzle bore 37. The velocity of the abrasive-laden fluid at the entrance to the nozzle 36 is much less than the speed of sound and has a Mach number much less than 1 (M<<1). The abrasive-laden fluid is directed through the elliptically converging section 44. As the abrasive-laden fluid exits the elliptically converging section 44 the fluid's velocity is approximately the speed of sound and has a Mach number approximately equal to 1 (M=1). The abrasive-laden fluid then enters and passes through the diverging expansion section 46. The velocity of the fluid as it exits the diverging expansion section 46 is about 1.4 times the speed of sound (M=1.4). After passing through the diverging expansion section 46 the abrasive-laden fluid enters and passes through the diverging compression section 48. The velocity of the fluid as it exits the diverging compression section 48 is approximately 1.7 times the speed of sound (M=1.7). The direction of flow of the abrasive-laden fluid as it exits the diverging compression section 48 is parallel and remains so as the fluid enters the parallel-flow particle-acceleration section 50. The particles within the fluid may not reach the velocity of the fluid but may be accelerated in the parallel-flow section 50 to higher velocities than the velocities of the particles at the entrance of the nozzle 36.

A fluid velocity having a Mach number of about 1.70 at the nozzle exit can be achieved assuming that the nozzle inlet conditions of the abrasive-laden fluid are constant. Examples of such nozzle inlet conditions include a reservoir stagnation pressure of approximately 75 psig, a static back pressure of approximately 14.7 psi, a reservoir stagnation temperature of about 57° C., and a fluid specific heat ratio of approximately 1.4. Reservoir stagnation pressure is the pressure at the exit bore 32.

A nozzle with the above dimensions and inlet conditions produces a resulting abrasive-laden static flow temperature at the nozzle exit of approximately 32° C. (89.6° F.). The body temperature of most humans is approximately 37° C. (98.6° F). Therefore, the abrasive-laden fluid will feel only slightly cool against, for example, a patient's tooth. This fluid temperature is obtained passively or without the use of an in-line heater or additional heating methods.

It is to be understood that a CD nozzle for use on biological organisms can be designed to produce an abrasive-laden fluid beam with various predetermined characteristics such as velocity, static flow temperature, and shape for other uses. This may be achieved by changing the specific dimensions of the internal contour of the nozzle bore 37. Additionally, such predetermined characteristics may be achieved by changing the operating conditions.

For example, in some applications it may be necessary to adjust the static flow temperature of the abrasive fluid beam. This adjustment can be achieved by varying the reservoir stagnation pressure. Reducing the reservoir stagnation pressure increases the fluid velocity inside the nozzle. As fluid passes through a supersonic nozzle a normal shock wave is produced through which the fluid passes. The fluid is heated as it travels through the shock wave. The rise in temperature of the fluid is proportional to the velocity of the fluid as it travels through the shock wave. Thus, the temperature of the fluid is increased as the fluid velocity increases. Likewise, fluid temperature decreases as the fluid velocity decreases. It can be seen that adjustment of the fluid pressure changes the fluid velocity which in turn changes the fluid temperature. Thus, if the static flow temperature of the abrasive fluid beam is about 32° C. (89.6° F.) with a reservoir stagnation pressure of about 75 psig and it is desirable to have a higher or lower static flow temperature, the reservoir stagnation pressure can be adjusted above and below 75 psig to produce the desired static flow temperature.

In addition, the shape of the abrasive fluid beam can be changed by adjusting the reservoir stagnation pressure. For example, when the nozzle inlet conditions are constant and the nozzle inlet stagnation pressure is higher than 75 psig, ($P_0$>75 psig) the fluid flow will be under-expanded and will pass through a Prandtl-Meyer (PM) expansion fan. The PM fan will tend to make the abrasive air stream spread out or diverge and accelerate as it moves away from the nozzle exit. This will result in a fluid beam having a relatively large cross-section. Thus, the fluid beam may be directed onto a relatively wide surface area of, for example, a dental patient's tooth. But the increased velocity of the particles will increase the mass removed per unit of time of the cutting speed only slightly so that the increase in cutting time will not be proportional to the cross-sectional area of the holes produced.

At nozzle inlet stagnation pressures below 75 psig but above 23 psig, ($23<P_0<75$ psig), fluid in the nozzle bore 37 expands to have a fluid pressure below room pressure. In order for the pressure of the fluid to rise to room pressure the fluid must pass through oblique shocks and will have an overexpanded flow. Thus, the fluid flow will pass through oblique shocks emanating from the edge of the nozzle exit. These shocks will tend to keep the abrasive particles within the fluid moving parallel to each other.

When the pressure is in the low end of the range (i.e. from about 40 psig to 23 psig) a focusing effect may be induced such that the abrasive particles actually converge to a point. This will result in faster depth per unit of time of cutting speeds to obtain pin-point accuracy. Thus, a CD nozzle is superior over prior nozzles for removing material from biological organisms.

The inside contour of the nozzle tip 36 is designed according to a computer program employing the Method of Characteristics as explained by Maurice J. Zucrow and Joe D. Hoffman, Volume II, Gas Dynamics, Multidimensional Flow; John D. Anderson, Modern Compressible Flow With Historical Perspective (2d Ed.); B. K. Hodge and Keith Koening, Compressible Fluid Dynamics With Personal Computer Applications.

The internal contour of the preferred embodiment of the nozzle 36 is corrected for the effects of boundary layer development. It is well known in fluid dynamics that a boundary layer is a very thin layer of slow moving fluid near the surface of any object over which the fluid flows. Boundary layer thickness increases with distance and in nozzles with very small internal bores, such as those employed in the present invention, the boundary layer will eventually grow in thickness until all the fluid in the nozzle "feels" the viscous effects. Since the internal bore of the nozzle of the present invention is very small, any boundary layer growth is detrimental to the operation of the tool because the boundary layer tends to "clog" the bore which adversely affects the velocity of the air stream.

The nozzle of the present invention has an internal contour that is corrected for the boundary layer development. This was achieved by computing the ideal shape of the nozzle by ignoring the viscous effects of the air fluid. From this ideal shape, a compressible boundary layer approximation is computed. The ideal shape is then adjusted to account for the presence of the boundary layer. This produces the final shape of the internal contour of the nozzle. Correction of fluid boundary layers can be achieved in a manner explained by Maurice J. Zucrow and Joe D. Hoffman, Volume II, Gas Dynamics, Multidimensional Flow.

Figure 7:
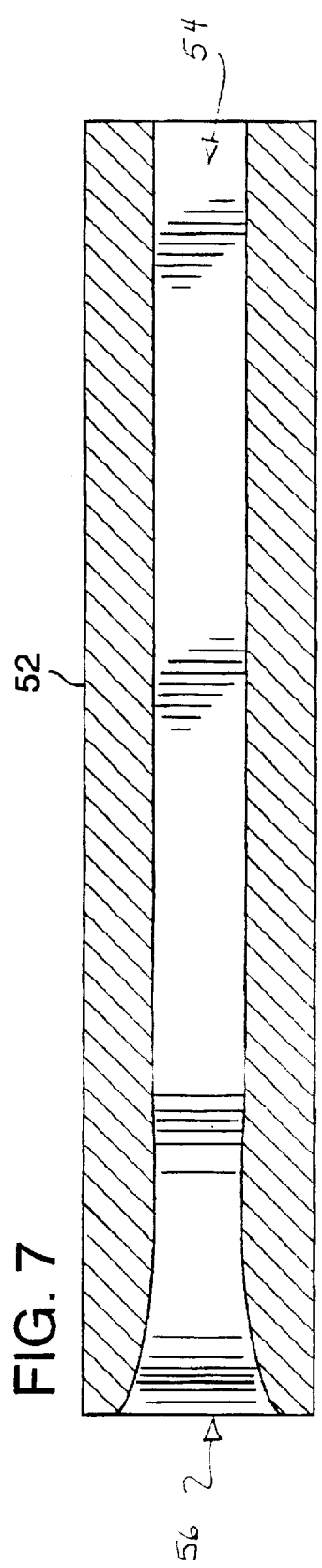
FIG. 7 is cross-sectional top view of the planar nozzle.
Figure 8:
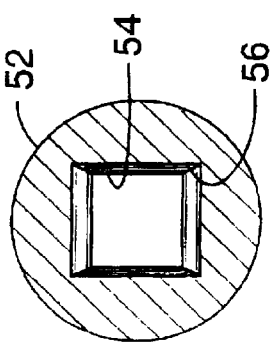
FIG. 8 is cross-sectional end view of the planar nozzle.
Figure 9:
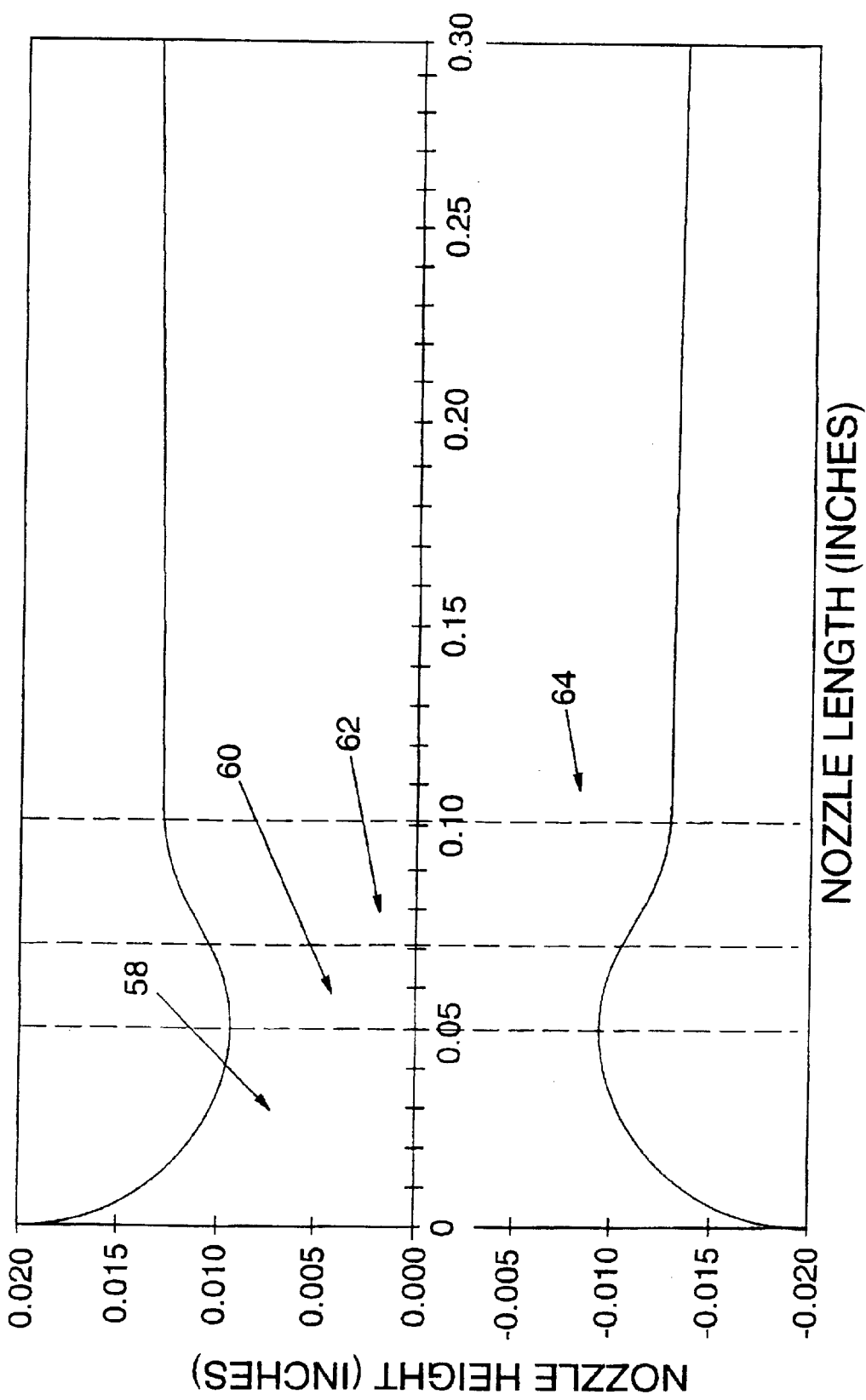
FIG. 9 is a graphic representation of the internal contour of the planar nozzle as seen in FIG. 6 shown exaggerated for clarity.
Figure 10:
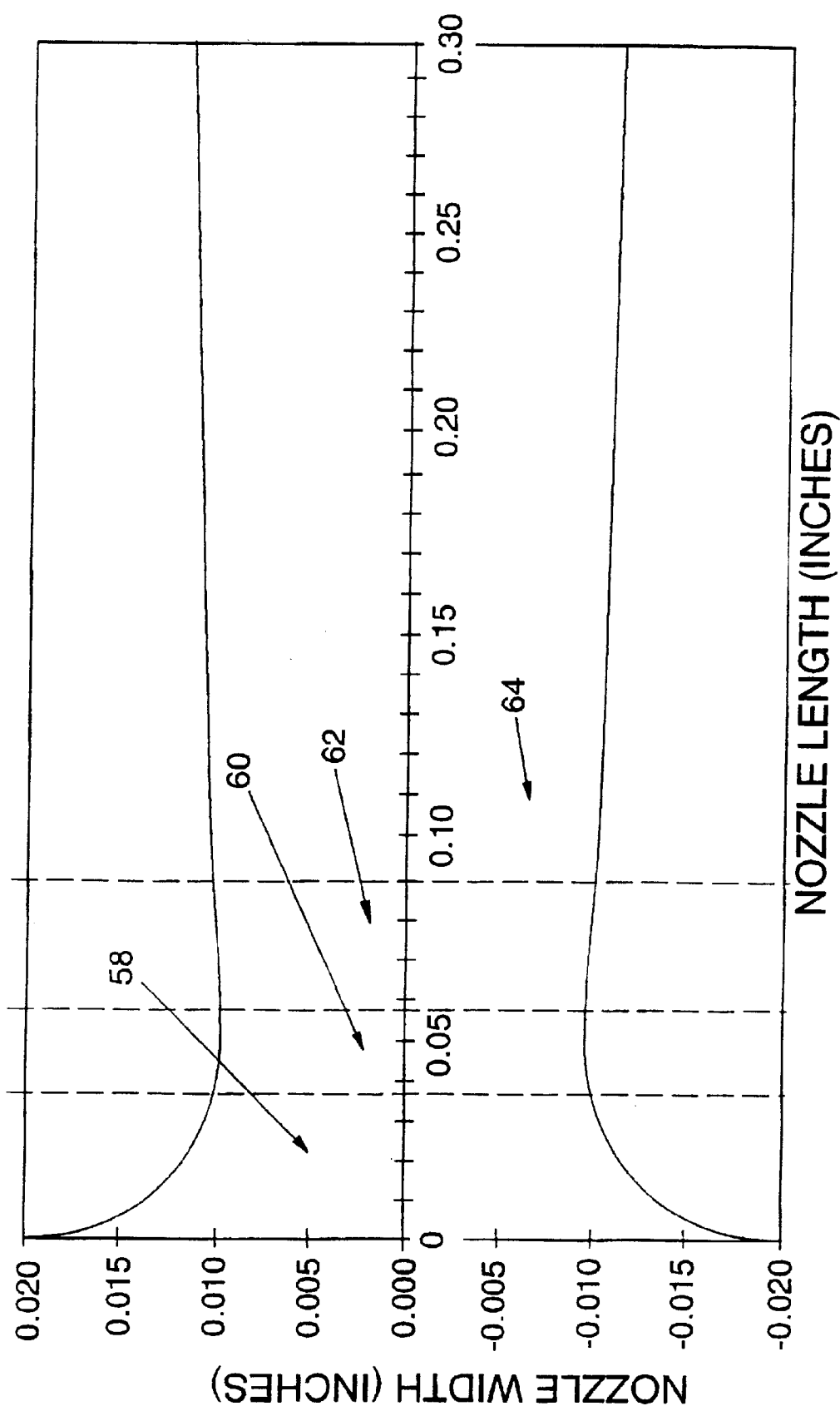
FIG. 10 is a graphic representation of the internal contour of the planar nozzle as seen in FIG. 7 shown exaggerated for clarity.

Referring now to FIGS. 6–10, a planar nozzle 52 is shown that can be produced by the above-mentioned methods having a variable bore 54 with a substantially rectangular cross-section. As seen in the graphical representation of FIGS. 9 and 10, the nozzle bore 54 is made up of four distinct sections that the abrasive-laden fluid must pass through in succession. The velocity of the abrasive-laden fluid at the entrance 56 to the nozzle 52 is much less than the speed of sound (M<1). First, the abrasive-laden fluid passes through an elliptically converging section 58 that has a length of about 0.05 inches (1.27 mm). As the abrasive-laden fluid exits the elliptically converging section 58 the velocity of the fluid is approximately the speed of sound (M=1). After passing through the elliptically converging section 58 the abrasive-laden fluid enters a diverging expansion section 60 which is about 0.02 inches (0.51 mm) long. The velocity of the abrasive-laden fluid increases within the diverging expansion section 60 and reaches a velocity of about 1.4 times the speed of sound (M=1.4) as the fluid exits the diverging expansion section 60. After passing through the diverging expansion section 60 the fluid enters a diverging compression section 62 that is about 0.04 inches (1.02 mm) long and reaches a fluid velocity of about 1.7 times the speed of sound (M=1.7). After passing through the diverging compression section 62 the fluid enters into a parallel flow section 64. The parallel flow section 64 extends the remaining length of the nozzle 52 and produces fluid velocity having a Mach number of about 1.7. The total length of the nozzle 52 is preferably about 0.30 inches (7.62 mm).

The configuration of the internal contour of the nozzle tip 52 is designed by the above-mentioned method of characteristics and boundary layer correction method. The abrasive fluid beam that exits the nozzle 52 is a substantially rectangular shape which can be used for removing a wide path of material such as for cleaning teeth. As with the nozzle 36, producing a fluid flow velocity having a Mach number of about 1.7 assumes that nozzle inlet conditions are constant.

The nozzle 52 produces a fluid beam having a temperature of approximately 32° C. (89.6° F.) which can be adjusted by changing the reservoir stagnation pressure in the manner discussed above with reference to nozzle 36. While the present invention has been particularly described in terms of specific embodiments thereof, it will be understood that numerous variations of the invention are within the skill of the art and yet are within the teachings of the technology and the invention herein. Accordingly, the present invention is to be broadly construed and limited only by the scope and spirit of the following claims.

What is claimed is:

1. A method of performing a dental procedure on a person's teeth by applying to the teeth a stream of abrasive-laden fluid combining abrasive particles with air exiting a converging-diverging nozzle with supersonic velocity that reaches the teeth at a temperature comfortable to the person.

2. The method of claim 1 wherein the dental procedure is performed at a comfortable temperature without the use of external temperature-control elements.

3. The method of claim 2 wherein the external temperature-control elements are selected from the group consisting of heaters, coolers, and anesthetics.

4. The method of claim 1 wherein the dental procedure is the cleaning of teeth.

5. The method of claim 1 wherein the dental procedure is removing tooth decay.

6. The method of claim 1 wherein the dental procedure is preparing the teeth to receive fillings.

7. A method of performing an air abrasion dental procedure on a person's teeth by applying an abrasive laden stream from an instrument equipped with a nozzle whose internal contour comprises a plurality of sections, each section manipulating the abrasive-laden stream to reach a velocity above Mach 1.0 at a temperature comfortable to the person.

8. The method of claim 7 wherein the plurality of sections include an elliptically converging section, a diverging expansion section, diverging compression section, and a parallel flow section.

9. The method of claim 7 wherein the abrasive-laden stream is aluminum oxide with an average particle size of about 27.5 microns.

10. The method of claim 7 wherein the dental procedures are selected from the group consisting of the cleaning of teeth, removing tooth decay, and preparing a tooth to receive fillings.

11. The method of claim 7 wherein the dental procedures are performed without pain, discomfort, or undue stress to the patient.

12. A method of removing material from a biological organism, comprising providing a source of pressurized abrasive-laden fluid that is directed through a converging-diverging bore of a device having a nozzle that receives and dispenses said fluid to a surface said method further comprising the steps of
  i: compressing the abrasive fluid through a converging inlet section of the bore to produce a substantially sonic flow velocity,
  ii: increasing the velocity of the abrasive fluid through a diverging expansion section of the bore,
  iii: compressing the abrasive fluid through a diverging compression section of the bore to produce parallel fluid flow, and
  iv: maintaining parallel fluid flow through a parallel flow section of the bore.

13. The method of claim 12 wherein the biological organism is a person.

14. The method of claim 13 wherein the material removed from the person is undesirable dental material from teeth.

15. A method of performing an air abrasion dental procedure by applying to a person's tooth an abrasive-laden stream from a nozzle tip having four sections that the abrasive-laden stream passes through in succession, the first section being an elliptically converging wall section, the second section being a diverging expansion wall section, the third section being a diverging compression wall section, the fourth section being a parallel-flow particle acceleration wall section.

* * * * *